...

United States Patent [19]

Davis

[11] Patent Number: 4,773,421

[45] Date of Patent: * Sep. 27, 1988

[54] RETENTION SUTURE APPARATUS

[76] Inventor: Emsley A. Davis, 1616 Colcord Ave., Waco, Tex. 76707

[*] Notice: The portion of the term of this patent subsequent to May 26, 2004 has been disclaimed.

[21] Appl. No.: 24,683

[22] Filed: Mar. 11, 1987

Related U.S. Application Data

[63] Continuation-in-part of Ser. No. 836,992, Mar. 6, 1986, Pat. No. 4,667,675.

[51] Int. Cl.$^4$ ............................................. A61B 17/08
[52] U.S. Cl. ................................ 128/335; 128/334 C; 128/337; 24/71.1
[58] Field of Search .............. 128/335, 334 C, 334 R, 128/337; 24/71.1, 71.2

[56] References Cited

U.S. PATENT DOCUMENTS

| | | | |
|---|---|---|---|
| 3,650,274 | 3/1972 | Edwards et al. | 128/335 |
| 3,695,271 | 10/1972 | Chodorow | 128/335 |
| 3,831,608 | 8/1974 | Kletschka et al. | 128/335 |
| 3,931,821 | 1/1976 | Kletschka et al. | 128/335 |
| 4,535,772 | 8/1985 | Sheehan | 128/335 |

Primary Examiner—Richard C. Pinkham
Assistant Examiner—Gary Jackson
Attorney, Agent, or Firm—Arthur F. Zobal

[57] ABSTRACT

A retention suture apparatus for maintaining a wound closed with a retention suture. The apparatus includes a relatively flat and stiff bridging member adapted to be placed across the wound. One end of the bridging member is adapted to have one end of the suture coupled thereto with the suture extending through the skin on one side of the wound, passing transversely to the wound under the skin and tissue and exiting from the skin on the other side of the wound such that its free end may engage the other end of the bridging member. A plurality of apertures are formed through the bridging member. The apparatus also includes a fastening member having a main body and a band. The main body has a hook fixed at one end and a wrapping projection extending transversely from its upper side. A channel extends longitudinally outward from the central portion of the main body to the other end of the main body where the channel forms an opening. The band, which has a hook fixed to one end, may be located within the channel and moved to different positions to shorten or lengthen the fastening member. The free end of the suture is wrapped around the projection and then tied to the fastening member. The fastening member is removably coupled to the bridging member by locating its hooks in selected apertures of the bridging member.

19 Claims, 4 Drawing Sheets

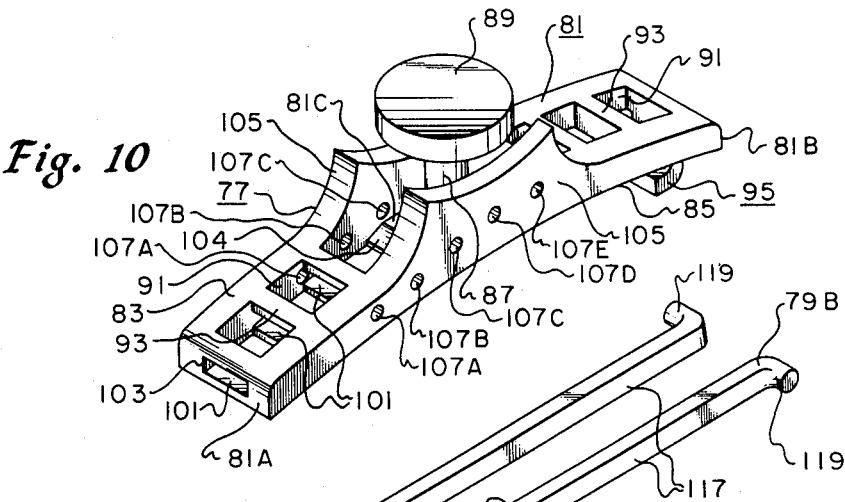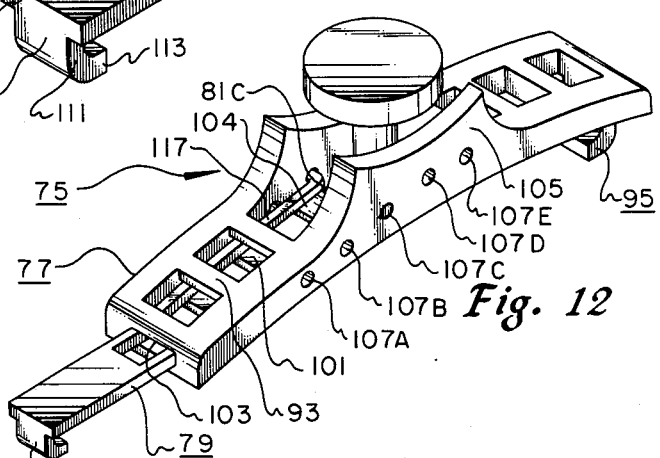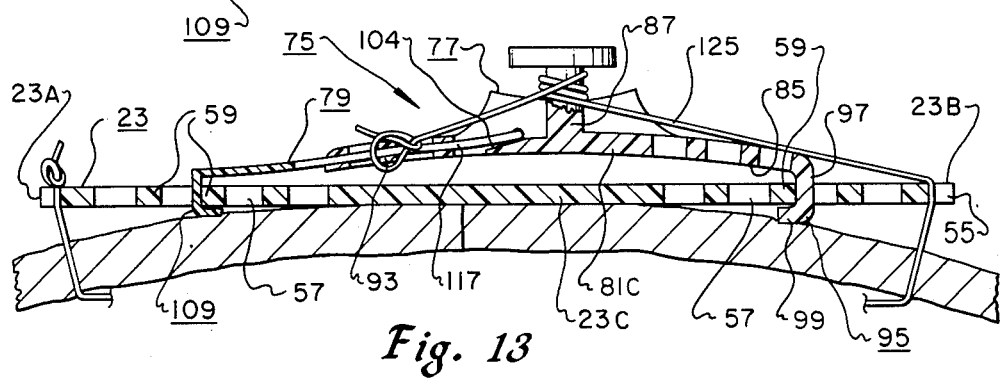

RETENTION SUTURE APPARATUS

This application is a continuation-in-part of my copending application, Ser. No. 06/836,992, filed Mar. 6, 1986, now U.S. Pat. No. 4,667,675.

FIELD OF INVENTION

The present invention relates to surgical devices, particularly those devices that are used in conjunction with retention sutures.

DESCRIPTION OF THE PRIOR ART

In abdominal surgery, complications concerning wound dehiscence can arise after the surgical incision has been stitched closed. When a wound dehisces, or bursts open, a potentially fatal situation results, particularly in high risk patients. Retention sutures placed transversely across the wound are used to prevent the occurrence of wound dehiscence by promoting wound closure. A single retention suture generally penetrates the skin and the several adjacent tissue layers at a point several centimeters to one side of the wound. The retention suture then traverses through the abdominal tissues, crosses the wound, and finally emerges on the opposite side of and several centimeters away from the wound.

While retention sutures solve some problems of abdominal surgery, several new problems are created. As the wound area swells, the tension of the suture increases, often resulting in damage to the underlying skin. Buttons and soft rubber tubes are prior art devices that are used to raise the sutures off of the skin and distribute the tension over a larger skin area. Buttons, however, do not prevent skin damage, while rubber tubes increase the difficulty of suture removal, among other problems.

Another prior art device, exemplified by U.S. Pat. No. 3,650,274, is the retention suture bridge. A retention suture bridge spans the wound and distributes the pressure caused by the suture over a larger area of skin than do buttons and tubes, thereby greatly alleviating the problems caused by high suture tension. In addition, to distribute the pressure of suture tension over a relatively larger area, several other aspects are desirable in a bridging device. Adjustments of suture tension are frequently necessary, therefore a retention suture bridge device should provide for tension adjustment with a minimum of difficulty. Further, since retention suture bridges cover the wound, periodic removal is required to allow access to the wound area for inspection and treatment. Thus, a retention suture bridge device should lend itself to removal and replacement.

This continuation-in-part application is directed to further developments concerning retention suture apparatuses. In this application, there is disclosed an embodiment of a retention suture apparatus, which is characterized in that the length of the upper or fastening member may be changed in order to accommodate different sized patients. FIGS. 10-13 of the drawings pertain particularly to the subject matter of this continuation-in-part application.

SUMMARY OF THE INVENTION

It is an object of the invention to provide a retention suture apparatus that can easily accommodate different sized patients.

The retention suture apparatus of the invention comprises a bridging member having two ends with a central portion intermediate its two ends and two opposite facing sides. The bridging member is adapted to be placed across the wound such that one of its sides faces the skin of the patient and its ends are on opposite sides of the wound with the central portion above the wound. One of the ends of the bridging member is adapted to have one end of a retention suture coupled thereto with the suture extending through the skin on one side of the wound, passing through the wound under the skin and tissue, exiting from the skin on the other side of the wound such that it may engage the other end of the bridging member. Fastening means is provided comprising a main body and movable means adapted to be coupled thereto. The main body has two ends and first and second opposite facing sides. Projection means extends transversely from the first side of the main body intermediate its ends. The main body has first coupling means adapted to be removably coupled to the bridging member. The movable means has second coupling means spaced from the first coupling means when the movable means is coupled to the main body. The second coupling means is adapted to be removably coupled to the bridging member. The first and second coupling means allows the fastening means to be removably coupled to the bridging member at two spaced apart positions with said first side and said projection means of the main body facing away from the bridging member whereby the suture may be extended from the other end of the bridging member to the projection means, wrapped around the projection means and the other end of the suture coupled to the fastening means. The movable means is movable relative to the two ends of the main body to vary the distance between said first and second coupling means.

In one aspect, the movable means is slidably coupled to the main body.

In a further aspect, the bridging member has a plurality of apertures formed therethrough on each side of its central portion. Said first and second coupling means comprise first and second hooks adapted to be located in a selected pair of apertures formed on opposite sides of the central portion of the bridging member for coupling the fastening means to the bridging member.

In another aspect, the main body has a channel that extends longitudinally outward from a central portion of the main body and through one of the two ends of the main body. The movable means comprises a portion slidably located in the channel with its hook being located outside of the channel. The portion slidably located in the channel has securing means for securing the movable means to the main body at a desired position.

In a further aspect, the portion of the movable means located within the channel comprises two spaced apart arms forming a gap therebetween sufficient to receive the projection means as the movable means is moved into the channel a given distance. The ends of the arms have pegs extending laterally outward therefrom and the sides of the main body forming the channel have apertures for receiving the pegs whereby the movable means may be secured to the main body at a desired position.

BRIEF DESCRIPTION OF THE DRAWINGS

FIG. 10 is a schematic isometric view of the fastening member, shown without the band, in accordance with a preferred embodiment, which is the subject matter of this continuation-in-part application.

FIG. 11 is a schematic isometric view of the band.

FIG. 12 is a schematic isometric view of the assembled fastening member.

FIG. 13 is a schematic cross-sectional view showing the use of the retention suture apparatus of the invention.

DESCRIPTION OF THE EMBODIMENT OF FIGS. 1-9

Figure 1:
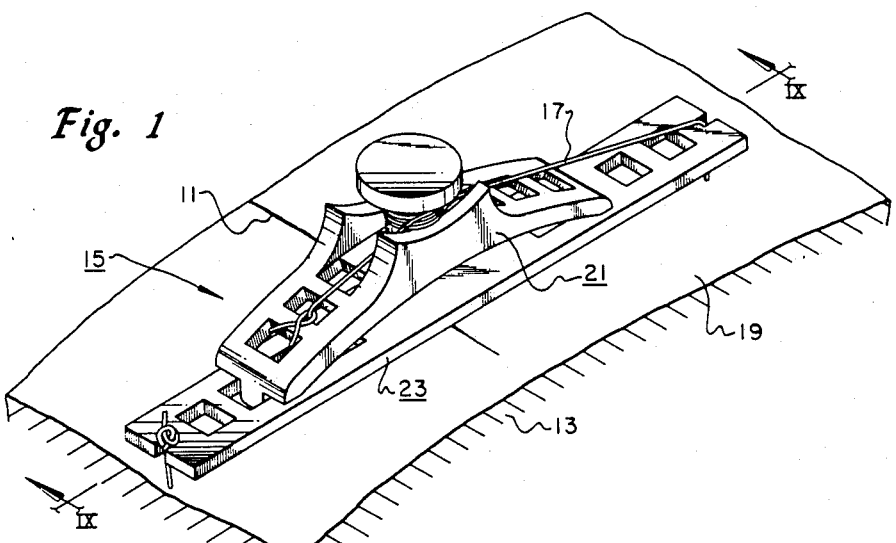
FIG. 1 is a schematic isometric view showing a surgical retention suture apparatus of the invention in place over a wound.
Figure 2:
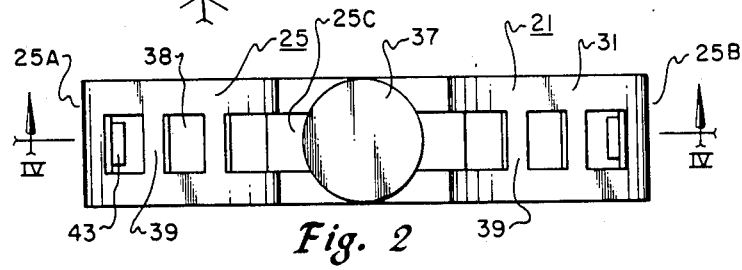
FIG. 2 is a top plan view of the fastening member of the apparatus.
Figure 3:
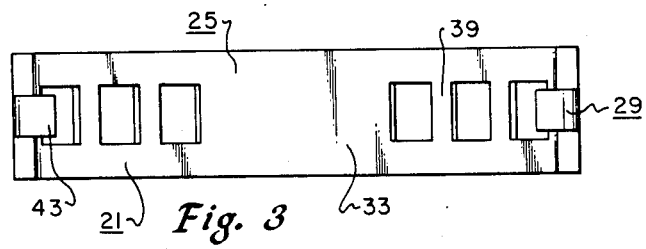
FIG. 3 is a bottom plan view of the fastening member.
Figure 4:
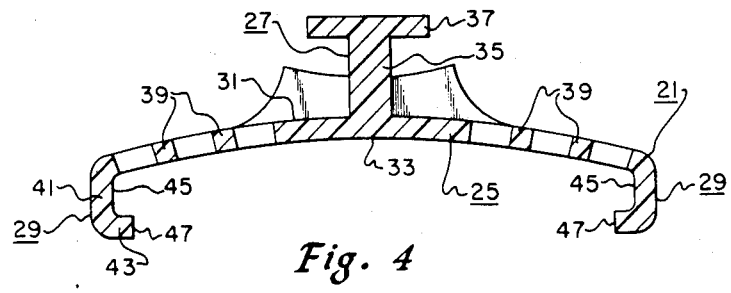
FIG. 4 is a longitudinal cross-sectional view taken at lines IV—IV of FIG. 2.

In FIG. 1, there is shown an isometric view of a portion of a wound formed by a surgical incision through abdominal tissues 13. Also shown is a surgical retention suture apparatus or device 15 of the invention and a retention suture 17 for closing the wound. The suture 17 is a flexible strand which may be formed of nylon. As shown in FIGS. 6-9, the suture 17 passes through the skin a short distance on each side of the wound 11 and beneath the skin through the tissue transverse to the wound in accordance with acceptable surgical practices. In a typical wound closure, several retention sutures 17, each held in place by one of the devies 15, will be utilized along the length of the wound.

The surgical retention suture apparatus 15 of the invention will now be described with particular reference to FIGS. 2-5. The surgical retention suture apparatus 15 includes a fastening member 21, a bridging member 23, and means for removably coupling the fastening member to the bridging member.

The fastening member 21 comprises a strip portion 25 which has two ends 25A and 25B and is normally arcuate or bowed from end to end forming a convex top surface 31 and a concave bottom surface 33. A wrapping projection 27 comprising a post or stem 35 and an enlarged head or cap 37 extends transversely from a central portion 25C of side 31 intermediate the end 25A and 25B. The post 35 is cylindrical in shape and the cap 37 is a round disc-like member. Three spaced apart apertures 38 are formed through the strip portion 25 on each side of the central portion 25C. Transverse struts 39 extend between adjacent apertures 38 on each side of the central portion 25C.

Hooks 29 each of which comprises a shank 41 and a curved portion 43, extend from the side 33 of the fastening member 21 at the ends 25A and 25B. The shanks 41 extend in a direction generally transverse to the length of the member 21 and the curved portions 43 curve toward each other terminating in surfaces 47 which face each other.

The fastening member is made of relatively flexible and resilient material such that the strip portion 25 may be straightened, to increase the distance between the surfaces 47 of the hooks 29, and then released wherein the strip portion 25 resumes its normal bowed or arcuate shape.

The bridging member 23 is an elongated strip having two ends 23A and 23B, a central portion 23C intermediate its ends, and opposite facing planar surfaces 51 and 53. The thickness of member 23 between surfaces 51 and 53 is uniform and is less than the length of the inboard surfaces 45 of the shanks 41 of the hooks 29 of member 21. Slots or notches 55 are formed in the member 23 at its ends 23A and 23B for use for retaining one end of the retention suture 17 and for guiding the suture 17 as it leaves the skin and extends to the fastening member 21. The bridging member 23 is made of a relatively stiff material such that when suture tension is applied to the end portions of the member 23, little deformity is experienced in the thin plane of the member between surfaces 51 and 53.

Figure 5:
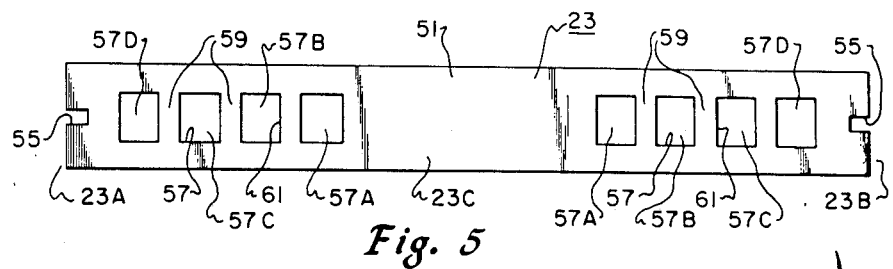
FIG. 5 is a plan view of the bridging member of the apparatus.
Figure 6:
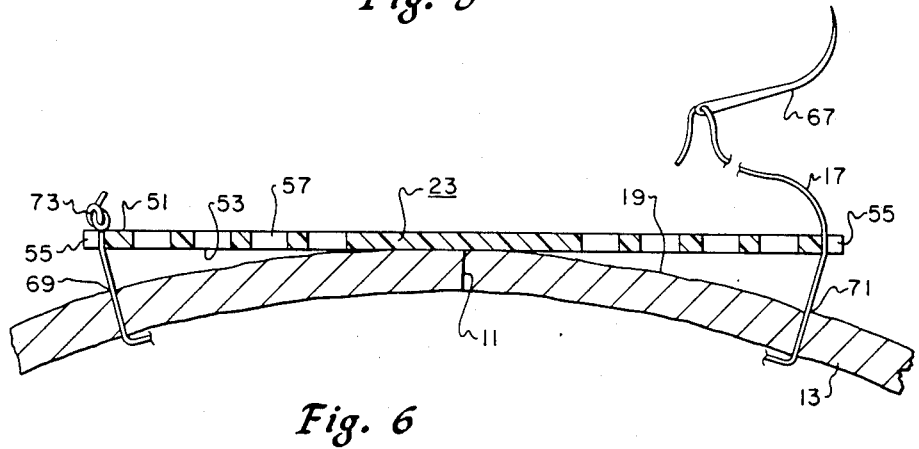
FIGS. 6-8 are schematic longitudinal cross-sectional views illustrating various steps in using the surgical retention suture apparatus FIG. 1.
Figure 8:
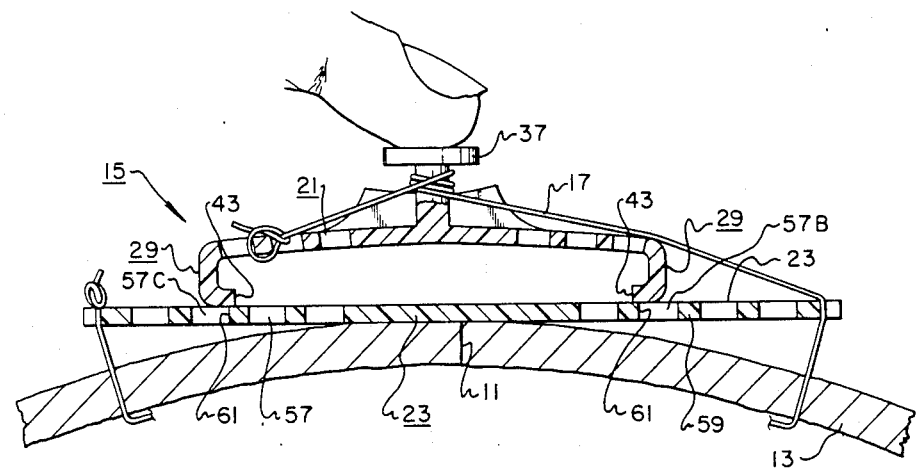
Figure 9:
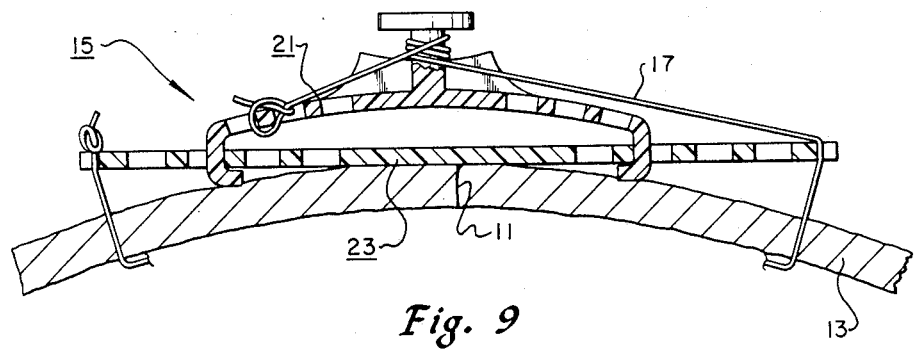
FIG. 9 is a schematic longitudinal cross-sectional view taken at lines IX—IX of FIG. 1.

The bridging member 23 has a plurality of longitudinally arranged rectangular shaped apertures 57 extending through the member 21 between surfaces 51 and 53 on each side of the center portion 23C of the member 23. Apertures 57 are spaced apart with transverse struts 59 extending between adjacent apertures 57 on each side of the central portion 23C. In FIG. 5, the apertures 57 on each side of the central portion 23C located progressively outward have been identified as 57A, 57B, 57C, and 57D. The apertures 57 each are of a size to allow the passage of the fastener hooks 29. The hooks 29 and bridging element struts 59 are sized to matingly engage each other. The apertures 57 and their struts 59 are arranged into sets for receiving the hooks 29, a set of apertures comprising one aperture on each side of the center portion 23C of the anchor piece 23. For example, as shown in FIG. 8, one set of apertures 57 is formed by apertures 57B and 57C. The distance between the outboard edges 61 of the struts of a set of apertures 57 is slightly less than the distance between the inboard surfaces 45 of the shank portions 41 of the fastener hooks 29 but greater than the distances between surfaces 47 of the hooks 29, when the fastening member 21 is in its normally bowed position.

The use of the retention suture apparatus 15 will now be described, with reference to FIGS. 6-9. A needle 67, attached to an end portion of a length of suture material 17, is passed through the skin 19 and underlying abdominal tissues 13 on one side of the wound 11 at a point of entry 69 which is located several centimeters away from the wound 11. After configuring the suture 17 through the abdominal tissues 13 in accordance with acceptable surgical practices, the needle 67 exits the abdominal tissues 13 and skin 19 at a point of exit 71 on the opposite side of the wound 11. The point of exit 71 of the suture 17 is located at approximately the same distance away from the wound 11 as is the point of entry 69.

The bridging member 23 is next laid transversely across the wound 11 and over the dressing sheets (not shown) with its surface 53 facing the skin 19. The member 23 is aligned with the retention suture 17 such that its slots 55 overlie a line intersecting the point of entry 69 and the point of exit 71 with the slots being 55 equidistant from the point of entry and the point of exit. The end of the suture 17 nearest the point of entry 69 is knotted in a large ball 73 and the suture is placed inside of the nearest slot 55 such that the knot is on the top surface 51 of the member 23. To keep the knot 73 from slipping through the retaining slot 55, the knot should be larger than the width of the slot. The needle end portion of the suture is then brought through the guide slot 55 at the other end of the number 23. The needle 67 is removed from the suture leaving a lengthy piece of suture remaining.

Figure 7:
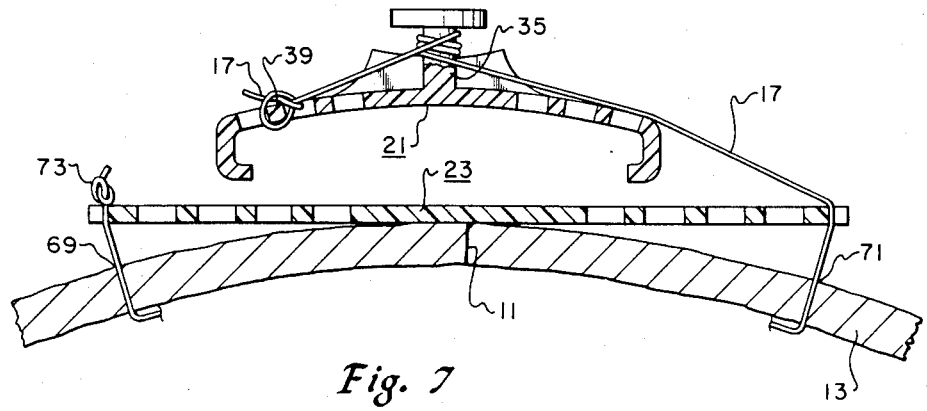

Next, the fastening member 21 is aligned with the bridging member 23 such that the surface 33 of member 21 faces the surface 51 of member 23 (see FIG. 7). The free end of the suture 17 is wrapped several times around the post 35 to achieve the desired suture tension. The free end of the suture is then tied to one of the struts 39 of the fastening member 21 on the side of the member 21 nearest the suture point of entry 69 into the skin.

With the hooks 29 of the fastening member 21 resting on the top surface 51 of the bridging member 23, downward force or pressure is applied to the cap 37 causing the fastening member 21 to straighten out (see FIG. 8). This in turn causes the distance between the inwardmost surfaces 47 of the hooks 29 to increase until it exceeds the distance between the outboard surfaces 61 of the struts 59 of the selected set of apertures 57. Usually one hook 29 will fall through an aperture 57 before the fastening member fully straightens out. This is followed by the other hook falling through the other aperture 57 of the set on the other side of the central portion 23C once the fastening member has been sufficiently straightened. When both hooks engage the outboard surfaces 61 of the struts 59 of the selected apertures 57, pressure is released from the cap, allowing the fastening member to regain its bowed shape. The fastening member 21 is now coupled or buckled in place to the bridging member 23 such that the position of the wrapping projection 27 relative to the guide slot 55 remains constant. The fastening member and the bridging member are locked together since the inboard surfaces 45 of the shank portions abut the outboard surfaces 61 of the struts 59 and the curved portions 43 are beneath the same struts (see FIG. 9). The fastening member may be removed or unbuckled from the bridging member by performing the above related steps in reverse order.

Several aspects of the invention will now be discussed. During the healing process, suture tension will usually have to be adjusted periodically. One method of adjusting suture tension by utilizing the surgical retention suture apparatus 15 is to unwind the suture a sufficient number of times from around the post 35 until the desired tension is achieved. In this adjustment method, the suture 17 may be untied from and then retied to the strut 39. Another method of adjusting the suture tension is to uncouple the fastening member 21 from the bridging member 23 and move the hooks 29 of the fastening member 21 into a different set of apertures 57 before recoupling.

Frequent cleaning and inspection of the wound is required thus necessitating the easy removal of the surgical retention suture apparatus 15. Once unbuckled from the bridging member, the fastening member can be laid aside with the suture still attached. The bridging member can be completely removed from the wound area by removing the suture ends from the slots or notches 55. Recoupling the ends of the suture is easily done. The ends of the suture need not be retied to achieve the proper tension since in this case the ends were not untied. Normally several retention suture bridges are spaced several centimeters apart along the length of the wound. In accessing the wound, every other retention suture bridge should be left intact to maintain the integrity of wound closure.

Another important aspect of the invention is that by using a bridging member of sufficient length so that the distance between the slots or notches 55 is just slightly longer than the distance between the point of entry and the point of exit, the angle of the suture to the skin as the suture emerges from the abdominal tissues is close to a right angle to avoid the suture cutting into the skin. This angle can be maintained on small adults or children by either using a shorter bridging member and a correspondingly smaller fastening member, or by tying one end of the suture to a fastening member strut 59 and passing the other end portion of the suture through an aperture 57 at the other end portion of the bridging member. Either of the surfaces 51 or 53 of the bridging member 23 can be employed to face the skin and the fastening member 21 can be coupled to the bridging member 23 such that its ends 25A and 25B are close to ends 23A and 23B or 23B and 23A respectively of member 23. Since the surface 51 or 53 of the stiff bridging member 23 that faces the skin is planar, the abdomen is allowed to expand and contract without being hampered by a rigid curved bridge device while maintaining a 90 degree angle between the suture and the moving skin.

Another important aspect of the invention is the use of the device to bring the wound edges together if a deficit had occurred as a result of extensive debridgement secondary to extensive wound infection.

In one embodiment the fastening member 21 and bridging member 23 may be formed of suitable teflon or other suitable plastic material.

DESCRIPTION OF THE EMBODIMENT OF FIGS. 10-13

In FIG. 13 there is shown a cross-sectional view of the retention suture apparatus of the present continuation-in-part application, in accordance with a preferred embodiment. The bridging member 23 is as described above. The fastening member 75 however, has been modified in order to allow the length of the fastening member to be changed so as to accommodate different sized patients. Small patients, such as children, may require shorter retention suture apparatuses than larger patients. A shortened bridging member can be fashioned from a longer bridging member either by cutting off the excess length or by threading the suture 125 through the apertures 57 instead of the end notches 55. With the shortened bridging member, a correspondingly shortened fastening member 75 is required. The fastening member 75 of the present continuation-in-part application has provision for increasing or decreasing its length. The fastening member 75 includes a main body 77 and a band 79.

Referring to FIG. 10, the main body 77 includes a strip portion 81 which has two ends 81A, 81B, a top surface 83, and a bottom surface 85. A wrapping projection comprising a post or stem 87 and an enlarged head or cap 89 extends transversely from a central portion 81C of the main body 77 intermediate the ends 81A, 81B. The post 87 is circular, although it may also be rectangular, in cross-section, and the cap 89 is a round disc-like member. The post 87 is spaced inward from the sides 105. Three spaced apart apertures 91 are formed through the strip portion 81 on each side of the central portion 81C. Transverse struts 93 extend between adjacent apertures 91 on each side of the central portion 81C.

A hook 95 extends from the bottom surface 85 of the main body 77 at one of the ends 81B. The hook 95, which is permanently fixed to the main body 77, has a shank 97 and a curved portion 99 (see FIG. 13). The shank 97 extends in a direction generally transverse to the length of the main body 77 and the curved portion 99 curves towards the central portion 81C of the main body.

A channel 101 extends longitudinally from the center portion 81C of the main body through the respective transverse struts 93 to the other end 81A where the channel forms an opening 103 (see FIG. 10). The portion of the channel 101 that extends through the transverse struts 93 is rectangular in cross-sectional shape and is centrally located between the main body top and bottom surfaces 83, 85 and between the sides 105 of the main body. The remainder of the channel 101 is formed by the top surface of the main body central portion 81C and the main body sides 105. The channel splits into two portions between the posts 87 and the two sides 105. The channel 101 has a size sufficient to receive the band 79. The end 104 of the main body central portion 81C nearest the channel opening 103 is beveled in order to allow the band 79 to emerge more easily from that portion of the channel which is located between the transverse struts 93 into that portion of the channel which is formed on top of the main body central portion, whenever the band is inserted far enough into the channel. Pairs of circular holes 107A, 107B, 107C, 107D and 107E extend through the sides 105 of the main body. Each pair of holes lies along a line that is perpendicular to the longitudinal axis of the main body, with a hole on each side of the longitudinal axis. The pairs of holes 107A, 107B, 107C, 107D and 107E are arranged longitudinally along the main body. The holes 107A and 107B communicate with that portion of the channel which is located between the transverse struts 93. The other holes 107C, 107D and 107E communicate with that portion of the channel which is on top of the main body central portion 81C. The distance between adjacent pairs of holes 107A, 107B, 107C, 107D and 107E is the same as the distance between adjacent transverse struts 59 in the bridging member 123.

The band 79 has two ends 79A, 79B and a rectangular cross-sectional shape that is substantially similar to the cross-sectional shape of the channel 101 (see FIG. 11). At one end 79A of the band is a hook 109 which has a shank 111 and a curved portion 113. The shank 111 extends in a direction generally transverse to the length of the band. The curved portion 113 curves towards the other end 79B of the band. A rectangular notch 115 extends from the other end 79B of the band 79 toward the hook end 79A of the band. The notch 115 bifurcates the other end 79B of the band into two arms 117. At the ends of the arms are cylindrical pegs 119 extending laterally outward in a perpendicular manner. The peg ends 79B of the arms 117 can be squeezed together and when released they return to their normal positions as shown in FIG. 11. The pegs 119 are shaped to be received by the circular holes 107A, 107B, 107C, 107D and 107E of the main body. The peg ends 79B of the arms 117 can be squeezed together to allow them to be inserted into the channel 101. When the pegs 119 are next to either of holes 107A, 107B, 107C, 107D or 107E, the arms 117 may be released to allow them to spring outward for insertion of the pegs 119 into the selected holes. The length of the band 79 is such that when the fastening member 79 is coupled to the bridging member 23 and the band 79 is locked into place within the main body 77 by the pegs 119, the hook 95 fixed to the main body 77 and the movable hook 109 will engage the respective transverse struts 59 of the bridging member (see FIG. 13).

The band 79 is inserted into the main body channel 101 peg end 79B first and with the hook 109 pointing downward (see FIG. 12) and with the peg ends of the arms squeezed together. The band 79, which slidably engages the channel 101, may be moved in and out to achieve the desired length of the fastening member 75. The position of the band 79 within the main body 77 is maintained by locating the pegs 119 into the appropriate pair of holes 107A, 107B, 107C, 107D or 107E. For the shorter lengths of the fastening member 75, the band 79 may be extended through the main body channel 101 to a position where the peg ends 79B of its arms 117 are on top of the main body central portion 81C. For even shorter lengths of the fastening member 75, the peg ends 79B of the arms 117 of the band 79 are able to extend past the post 87 between the sides 105. The transverse dimension of the post 87 between the sides 105 is small enough such that the arms 117 may be located on opposite sides of the post 87 between the sides 105 and squeezed together against the post 87 to position the pegs 119 next to holes 107D or 107E and released for insertion therein. Thus, the post 87 does not interfere with the movement of the band 79. Furthermore, the notch 115 in the band permits movement of the band 79 within the channel 101 even when a suture 125 is tied to one of the transverse struts 93.

The use of the fastening member 75 will now be described, with particular reference to FIG. 13. The suture 125 and the bridging member 23 are located in place as described above. The band 79 is positioned within the main body channel 101 so as to achieve the desired length of the fastening member 75, without yet engaging the pegs 119 into a pair of holes 107A, 107B, 17C, 107D or 107E. The free end of the suture 125 is wrapped several times around the post 87 to achieve the desired suture tension. The free end of the suture 125 is then tied to one of the struts 93 of the fastening member 75. While maintaining the desired suture tension, the fastening member hooks 95, 109 are placed within a set of apertures 57 of the bridging member 23. The band 79 is then moved toward the post 87 so that the hooks 95, 109 engage the bridging member struts 59. The band 79 is maintained in this position by engaging the pegs 119 into an appropriate pair of holes 107A, 107B, 107C, 107D or 107E. Disengagement of the fastening member 75 from the bridging member 23 is achieved by reversing the above steps, beginning with removal of the pegs 19 from the holes by squeezing the arms 117 together.

The essence of the invention is that the fastening member may be adjusted as required by patient size. For large patients, a long bridging member and a long fastening member may be used. For smaller patients, however, a shorter bridging member and consequently a shorter fastening member may be required. The bridging member can be easily shortened by cutting off any excess length. Such a procedure can be performed in an operating room during surgery. Alternatively, the bridging member can be effectively shortened by threading the suture through the bridging member apertures rather than the endmost notches. The length of the fastening member can just as easily be adjusted by sliding the band in the main body channel. The sliding movement of the band causes the movable hook to move along the longitudinal axis of the fastening member, thereby either increasing or decreasing the distance between the fastening member hooks. In addition, the sliding movement of the band allows for the installation and removal of the fastening member onto and from the bridging member without untying the suture from the fastening member. The band can be slid outwardly away from the post so as to increase the distance between the two hooks and allow the hooks to enter the apertures of the bridging member. Then the band can be slid inwardly toward the post so as to decrease the distance between the two hooks and cause the hooks to engage the bridging member struts.

The band 79 may be formed of suitable Teflon or other suitable plastic material.

The foregoing disclosure and the showings made in the drawings are merely illustrative of the principles of this invention and are not to be interpreted in a limiting sense.

I claim:

1. Apparatus for use with a retention suture for maintaining a wound of a patient closed, comprising: a bridging member having two ends with a central portion intermediate its two ends, and two opposite facing sides,
   said bridging member being adapted to be placed across the wound such that one of its sides faces the skin of the patient and its ends are on opposite sides of the wound with said central portion above the wound,
   one of said ends of said bridging member being adapted to have one end of a retention suture coupled thereto with the suture extending through the skin on one side of the wound, passing transversely to the wound under the skin and tissue, and exiting from the skin on the other side of the wound such that it may engage the other end of said bridging member,
   fastening means comprising a main body and movable means adapted to be coupled thereto,
   said main body having two ends and first and second opposite facing sides,
   projection means extending transversely from said first side of said main body intermediate its ends,
   said main body having first coupling means adapted to be removably coupled to said bridging member,
   said movable means having second coupling means spaced from said first coupling means when said movable means is coupled to said main body,
   said second coupling means being adapted to be removably coupled to said bridging member,
   said first and second coupling means allowing said fastening means to be removably coupled to said bridging member at two spaced apart positions with said first side and said projection means of said main body facing away from said bridging member whereby the suture may be extended from said other end of said bridging member to said projection means, wrapped around said projection means and the other end of the suture coupled to said fastening means,
   said movable means being movable relative to said two ends of said main body to vary the distance between said first and second coupling means.

2. The apparatus of claim 1, wherein said movable means is slidably coupled to said main body.

3. The apparatus of claim 2, wherein said movable means is extendable from one of said two ends of said main body.

4. The apparatus of claim 2, comprising:
   slots formed in said two ends of said bridging member for receiving the suture as it passes through the skin.

5. The apparatus of claim 2, wherein said projection means comprises a stem fixed to said fastening member.

6. The apparatus of claim 2, comprising at least one suture receiving aperture extending through said main body between its first and second sides whereby the other end of the suture, after being wrapped around said projection means, may be inserted through said suture receiving aperture and tied to said main body.

7. The apparatus of claim 2, wherein said bridging member is made of a relatively stiff material and said one side of said bridging member is planar.

8. The apparatus of claim 2, comprising:
   slots formed in said two ends of said bridging member for receiving the suture as it passes through the skin,
   said projection means comprising a stem fixed to said fastening member,
   at least one suture receiving aperture extending through said main body between its first and second sides whereby the other end of the suture, after being wrapped around said projection means, may be inserted through said suture receiving aperture and tied to said main body,
   said bridging member is made of a relatively stiff material and said one side of said bridging member is planar.

9. The apparatus of claim 1, wherein said movable means is extendable from one of said two ends of said main body.

10. The apparatus of claim 1, wherein:
    said bridging member has a plurality of apertures formed therethrough on each side of said central portion,
    said first and second coupling means comprising first and second hooks respectively adapted to be located in a selected pair of apertures formed on opposite sides of said central portion of said bridging member for coupling said fastening means to said bridging member.

11. The apparatus of claim 10, wherein:
    said movable means is slidably extendable from one of said two ends of said main body.

12. The apparatus of claim 10, wherein:
    said main body has a channel that extends longitudinally outward from a central portion of said main body and through one of said two ends of said main body,
    said movable means comprising a portion slidably located in said channel with said second hook being located outside of said channel,
    said portion slidably located in said channel having securing means for securing said movable means to said main body at a desired position.

13. The apparatus of claim 12, wherein:
    the sides of said channel have apertures that are longitudinally arranged along a portion of the length of said channel,
    said portion of said movable means having pegs that extend laterally outward therefrom wherein said pegs may be located in said apertures of said channel sides to secure said movable means to said main body at a desired position.

14. The apparatus of claim 12, wherein:

said portion of said movable means comprises two spaced apart arms forming a gap therebetween sufficient to receive said projection means as said movable means is moved into said channel a given distance.

15. The apparatus of claim 14, wherein:

the sides of said channel have apertures that are longitudinally arranged along a portion of the length of said channel, said securing means comprises pegs extending laterally outward from said arms wherein said pegs may be located in said apertures of said channel sides to secure said movable means to said main body at a desired position.

16. Apparatus for use with a retention suture for maintaining a wound of a patient closed, comprising:

a bridging member having two ends with a central portion intermediate its two ends, and two opposite facing sides, said bridging member being adapted to be placed across the wound such that one of its sides faces the skin of the patient and its ends are on opposite sides of the wound with said central portion above the wound, one of said ends of said bridging member being adapted to have one end of a retention suture coupled thereto with the suture extending through the skin on one side of the wound, passing transversely to the wound under the skin and tissue, and exiting from the skin on the other side of the wound such that it may engage the other end of said bridging member, a fastening member having a length bounded by two ends and having first and second opposite facing sides, said two ends lying along a longitudinal axis of said fastening member, projection means extending transversely from said first side of said fastening member intermediate its ends, said fastening member and said bridging member including means to allow said fastening member to be removably coupled to said bridging member such that said first side and said projecting means of said fastening member face away from said bridging member whereby the suture may be extended from said other end of said bridging member to said projection means, wrapped around said projection means and the other end of the suture coupled to said fastening member, said fastening member having means for changing the length of said fastening member by moving one of said ends along said longitudinal axis with respect to the other end.

17. Apparatus for use with a retention suture for maintaining a wound of a patient closed, comprising:

a bridging member having two ends with a central portion intermediate its two ends, and two opposite facing sides, said bridging member being adapted to be placed across the wound such that one of its sides faces the skin of the patient and its ends are on opposite sides of the wound with said central portion above the wound, one of the said ends of said bridging member being adapted to have one end of a retention suture coupled thereto with the suture extending through the skin on one side of the wound, passing transversely to the wound under the skin and tissue, and exiting from the skin on the other side of the wound such that it may engage the other end of said bridging member, a fastening member having a length bounded by two ends and having first and second opposite facing sides, said two ends lying along a longitudinal axis of said fastening member, projection means extending transversely from said first side of said fastening member intermediate its ends, said fastening member and said bridging member including means to allow said fastening member to be removably coupled to said bridging member such that said first side and said projecting means of said fastening member face away from said bridging member whereby the suture may be extended from said other end of said bridging member to said projection means, wrapped around said projection means and the other end of the suture coupled to said fastening member, said fastening member comprising a main body and a band, said main body has two ends and said projection means, said main body has a central channel that extends longitudinally outward from a central portion of said main body, said channel having a transverse cross-sectional shape and an opening for receiving said band, said channel opening being located at said other end of said main body, said band having two ends, one end of which has said means for removably coupling said fastening member to said bridging member, the other end of said band having means for coupling said band to said main body, said band having a transverse cross-sectional shape which is substantially similar to that of said channel, said band slidably engages said channel, wherein said band may be moved inside the channel to change the length of said fastening member.

18. Apparatus for use with a retention suture for maintaining a wound of a patient closed, comprising:

a bridging member having first and second ends with a central portion intermediate its ends and two opposite facing sides, said bridging member being adapted to be placed across the wound such that one of its sides faces the skin of the patient and its ends are on opposite sides of the wound with said central portion above the wound, said second end of said bridging member being adapted to have one end of a retention suture coupled thereto with the suture extending through the skin on one side of the wound, passing transversely to the wound under the skin and tissue, and exiting from the skin on the other side of the wound such that it may engage said first end of said bridging member, fastening means comprising a main body and movable means adapted to be coupled thereto, said main body having first and second ends and first and second opposite facing sides, projection means extending transversely from said first side of said main body intermediate its ends, coupling means formed at least on said movable means for removably coupling said fastening means to said bridging member such that said first side and said projection means of said main body face away from said bridging member whereby the suture may be extended from said first end of said bridging member to said projection means, wrapped around said projection means and the other end of the suture coupled to said fastening means, said fastening means when coupled to said bridging member having said first and second ends of said main body located closest to said first and second ends of said bridging member, respectively and with said coupling means of said movable means located closer to said second end of said bridging member than to said first end thereof, said movable means being movable relative to said first and second ends of said main body.

19. The apparatus of claim 18, wherein said movable means is slidably coupled to said main body.

* * * * *